(12) United States Patent
Trail et al.

(10) Patent No.: US 11,903,388 B2
(45) Date of Patent: Feb. 20, 2024

(54) LICHEN COMPOUNDS THAT INHIBIT MYCOTOXIN PRODUCTION

(71) Applicant: Board of Trustees of Michigan State University, East Lansing, MI (US)

(72) Inventors: Frances Trail, Mason, MI (US); Ludmila Roze, Okemos, MI (US); John E. Linz, Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 59 days.

(21) Appl. No.: 17/555,057

(22) Filed: Dec. 17, 2021

(65) Prior Publication Data

US 2022/0104501 A1    Apr. 7, 2022

Related U.S. Application Data

(63) Continuation of application No. 16/521,326, filed on Jul. 24, 2019, now abandoned.

(60) Provisional application No. 62/702,424, filed on Jul. 24, 2018.

(51) Int. Cl.
| | | |
|---|---|---|
| *A61K 39/00* | (2006.01) | |
| *A01N 65/00* | (2009.01) | |
| *C12Q 1/18* | (2006.01) | |

(52) U.S. Cl.
CPC ............. *A01N 65/00* (2013.01); *C12Q 1/18* (2013.01)

(58) Field of Classification Search
CPC .................................................... A01N 65/00
See application file for complete search history.

(56) References Cited

U.S. PATENT DOCUMENTS

2009/0048332 A1*   2/2009   Choudhary ............ A61K 36/09
                                                                514/568
2020/0029575 A1    1/2020   Trail et al.

OTHER PUBLICATIONS

"U.S. Appl. No. 16/521,326, Advisory Action dated Mar. 12, 2021", 3 pgs.
"U.S. Appl. No. 16/521,326, Examiner Interview Summary dated Oct. 20, 2020", 3 pgs.
"U.S. Appl. No. 16/521,326, Final Office Action dated Jan. 4, 2021", 10 pgs.
"U.S. Appl. No. 16/521,326, Final Office Action dated Sep. 20, 2021", 11 pgs.
"U.S. Appl. No. 16/521,326, Non Final Office Action dated Apr. 20, 2021", 9 pgs.
"U.S. Appl. No. 16/521,326, Non Final Office Action dated Jul. 8, 2020", 12 pgs.
"U.S. Appl. No. 16/521,326, Response filed Mar. 4, 2021 to Final Office Action dated Jan. 4, 2021", 9 pgs.
"U.S. Appl. No. 16/521,326, Response filed May 15, 2020 to Restriction Requirement dated Mar. 19, 2020", 7 pgs.
"U.S. Appl. No. 16/521,326, Response filed Jul. 20, 2021 to Non Final Office Action dated Apr. 20, 2021", 10 pgs.
"U.S. Appl. No. 16/521,326, Response filed Nov. 4, 2020 to Non Final Office Action dated Jul. 8, 2020", 10 pgs.
"U.S. Appl. No. 16/521,326, Restriction Requirement dated Mar. 19, 2020", 7 pgs.
Dulger, et al., "", Tr. J. of Biology vol. 22, (1998), 111-118.
Kosanic, et al., "", Pak. J. Pharm. Sci., vol. 24, No. 2, (2011), 165-170.
Litvinov, et al., "Batanicheski Zhurnal", Sankt-Peterburg, Russian Federation vol. 43, (1958), 557-560.
Ristic, et al., "Current Pharmaceutical Biotechnology", vol. 17, (2016), 1-8.
Shrestha, et al., "", Phytotherapy Research vol. 29, (2015), 100-107.
Solhaug, et al., "", Oecologia vol. 108, (1996), 412-418.

\* cited by examiner

*Primary Examiner* — Albert M Navarro
(74) *Attorney, Agent, or Firm* — Schwegman Lundberg & Woessner, P.A.

(57) ABSTRACT

Described herein are methods for obtaining useful compounds from lichens.

5 Claims, 7 Drawing Sheets

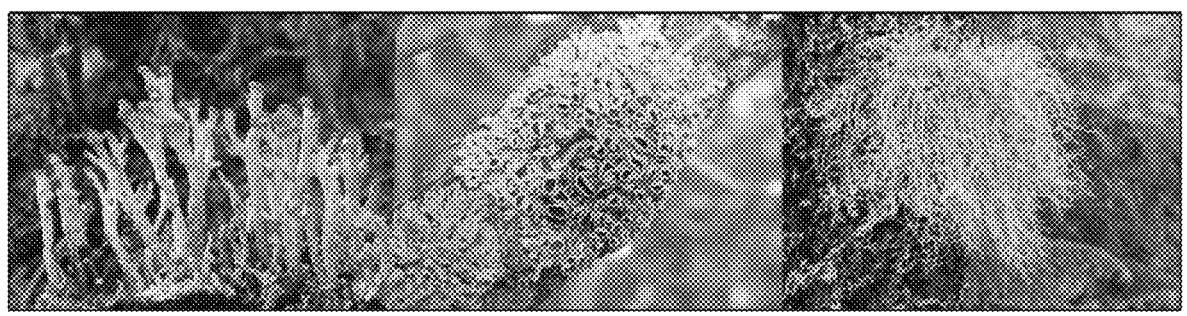
*Fig.1A*   *Fig.1B*   *Fig.1C*
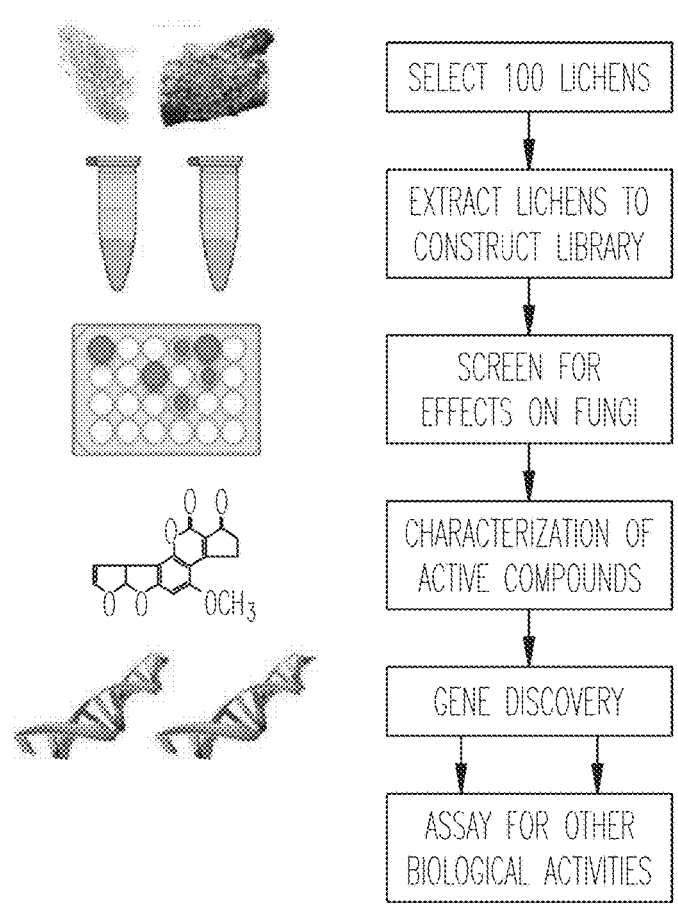
*Fig.1D*

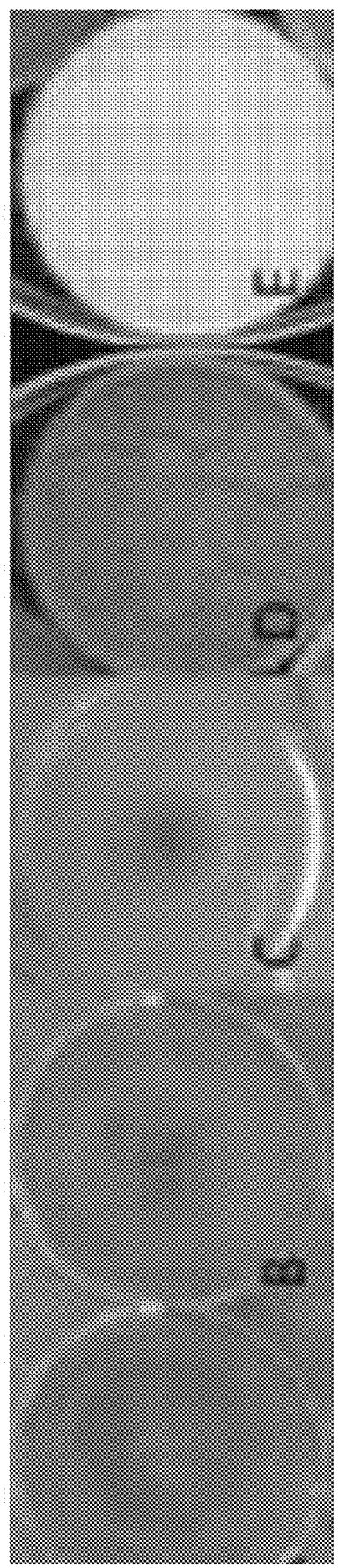

Fig. 3A
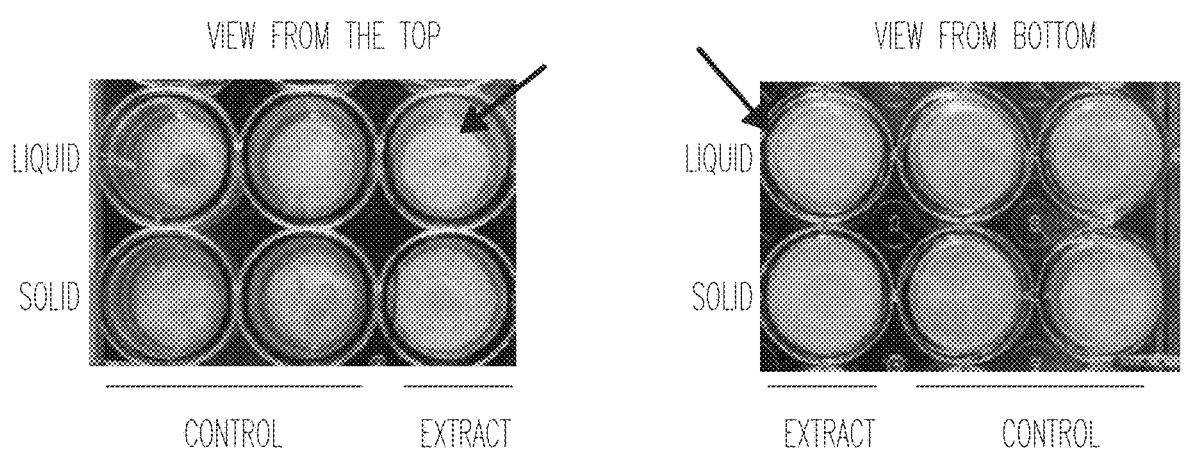
Fig. 3B
Fig. 3C

LICHEN COMPOUNDS THAT INHIBIT MYCOTOXIN PRODUCTION

RELATED APPLICATIONS

This application is a continuation of U.S. application Ser. No. 16/521,326, filed Jul. 24, 2019, which claims benefit of priority to the filing date of U.S. Provisional Application Ser. No. 62/702,424, filed Jul. 24, 2018, the contents of which are specifically incorporated herein by reference in their entity.

BACKGROUND OF THE INVENTION

Fungi pose a greater threat to plant and animal biodiversity than other types of pathogens (protists, viruses, bacteria, helminths), and the threat of fungi to ourselves, our food security, and our environment is increasing (Fischer et al., Nature 484:186-194 (2012)). Human diseases caused by fungi (mycoses) are on the rise concomitantly with the increase in numbers of people with immunosuppressive conditions (i.e. AIDS, organ transplants, cancer treatments). Infections of immunocompromised humans by fungi including *Aspergillus fumigatus* and *Cryptococcus neoformans* have increased due to their ability, which is fairly unique among fungi, to grow at body temperatures. Acquired drug resistance in medically relevant microorganisms, including fungi and bacteria, is another severe threat to human health. In addition, fungi and fungal-like organisms are responsible for the destruction of about 125 million tons of major crops such as rice, wheat, maize, potatoes, and soybeans each year.

History also shows that fungi and fungal-like organisms can dramatically affect human health and food security. For example, the Irish Potato Famine, which was caused by the late blight mold, resulted in mass starvation, and the death of 1 million people in the 1840s. More recently, a new strain of wheat rust from Africa, UG99 (Uganda 99), which causes up to 100% crop loss, is spreading across wheat growing regions of the world. Mycotoxins pose a threat to human health on nearly every continent, and climate change is shifting their appearance to new areas (Magan et al., Plant Pathology 60:150-163 (2011)).

Among mycotoxin contamination of crops, one of the most serious is aflatoxin contamination of crops. Aflatoxin is thought to be the most potent naturally occurring carcinogen known. An aflatoxin contaminated diet has been directly linked with elevated rates of liver cancer, decreased immunity, kwashiorkor, and growth stunting.

In western countries, amounts of aflatoxin contaminants in crops are regulated to below 10 parts per billion. However, outbreaks of aflatoxicosis are common in underdeveloped countries, mostly among poorly nourished rural populations whose staple food is maize. Large losses of crops contaminated with aflatoxin are common. Worldwide, *Aspergillus* species cause significant losses in major crops. The annual economic impact of aflatoxin contamination on corn and peanut agriculture in the United States is thought to exceed $1 billion dollars.

A second major class of mycotoxins is the trichothecenes, including T-2 toxin, nivalenol, deoxynivalenol, and diacetoxyscirpenol, produced by the fungi *Fusarium, Cephalosporium, Myrothecium, Stachybotrys* (the black mold), *Trichoderma*, and others. In western countries, levels of deoxynivalenol are advised to be less than 1 ppm for finished grain products for human consumption. The trichothecenes are also damaging to the health of pigs, cattle, poultry, and particularly swine. Due to climate change and global warming in recent years, mycotoxigenic fungi are altering their ranges, moving into areas in which they were not previously found.

SUMMARY

Described herein are methods that include extracting lichens and testing the extracts so obtained for their effects on fungal sporulation, fungal hyphal growth and fungal secondary metabolite production. Also described are antifungal compositions, as well as methods for determining the microbial source and the structure of the active compounds.

One method involves extracting a lichen sample with alcohol, ethyl acetate, acetone or a combination thereof to provide a lichen extract, and measuring whether the lichen extract inhibits the growth, sporulation, or mycotoxin production of a fungus.

Another method involves (a) extracting a lichen sample with alcohol, ethyl acetate, acetone or a combination thereof to provide a lichen extract; (b) mixing the extract, a component of the extract, or a compound obtained from the extract with *Aspergillus parasiticus* strain B62 cells to form an assay mixture; and (c) measuring whether growth, sporulation, or aflatoxin production by the *Aspergillus parasiticus* strain B62 cells is different from a control.

Another method involves extracting a lichen as in (a) described above, and (h) mixing the extract, a component of the extract, or a compound obtained from the extract with *Fusarium graminearum* to form an assay mixture; and (c) measuring whether growth or deoxynivalenol or 15-acetyl deoxynivalenol or nivalenol production of variations thereof by the *Fusarium graminearum* cells is different from a control.

The methods can be used to provide useful lichen extracts, compounds, or components of the extracts.

Compositions are also described herein that can include a carrier and an extract, compound, or a component of an extract obtained, for example, by the methods described herein.

Such compositions, extracts, compounds, and extract components are useful for inhibiting fungal growth, fungal sporulation, toxin production, or a combination thereof. For example, the compositions, extracts, compounds, and extract components can reduce mycotoxin or toxin production by at least 10%, at least 20%, at least 30%, at least 40%, at least 50%, at least 60%, at least 70% at least 80%, at least 90%, at least 95%, or at least 99%.

The extracts are stable, and retain the ability to inhibit fungal growth, fungal sporulation, fungal toxin production, or a combination thereof for at least ten years, or at least 20 years, or at least 30 years.

The compositions, extracts, compounds, and extract components can be applied to structures, surfaces, agricultural crops, storage bins, storage facilities, animal feed, plant seeds, nuts, plant parts, plant products, or a combination thereof. The compositions, extracts, compounds, and extract components can be applied to surfaces in bathrooms, kitchens, closets, basements, attics, entryways, cabinets, boats, hams, animal shelters, warehouses, food storage facilities, and other such surfaces. The compositions, extracts, compounds, and extract components can be applied to grain-producing plants, nut-producing plants, vegetable-producing plants, fruit-producing plants, starch-producing plants, fiber-producing plants, fodder-producing plants, grains, nuts, vegetables, fruits, starch, fibers, flour, fodder, leaves, stock, seeds, oil, or a combination thereof. The compositions, extracts, compounds, and extract components can be applied to almonds, barky, betel nuts, brazil nuts, cashews, chestnuts, coconut, coffee, corn, flour, hazelnuts, macadamia nuts, oats, pecans, peanuts, pine nuts, pistachios, rice, rye, sesame seeds, soybean, spices, walnuts, wheat, or combinations thereof.

Such methods can reduce the mycotoxin, fungal spore, or fungal content in the surfaces, agricultural crops, storage bins, storage facilities, animal feeds, plant seeds, nuts, plant parts, plant products, or other places.

DESCRIPTION OF THE FIGURES

FIG. 1A-1D illustrate some types of lichens and a method for assaying lichens to isolate bioactive lichen compounds with novel activities. FIG. 1A shows an image of *Cladonia* spp. lichens that grow on the soil. FIG. 1B shows an image of *Physica* spp. lichens that attach to tree branches. FIG. 1C shows an image of *Usnea* spp. lichens that attach to branches. FIG. 1D is a schematic diagram illustrating methods for isolating bioactive lichen compounds with novel activities.

FIG. 2A-2E illustrate high through-put assays in 24 well plates for antifungal effects of lichen extracts on the fungus *Aspergillus parasiticus* strain 1362. The orange-red pigment is a precursor and indicator of aflatoxin production. FIG. 2A shows a 3-day old culture of *Aspergillus parasiticus* strain B62 that was not treated (control), FIG. 2B shows a 3-day old culture of *Aspergillus parasiticus* strain B62 treated with an aflatoxin biosynthesis inhibitor, FIG. 2C shows a 3-day old culture of *Aspergillus parasiticus* strain B62 treated with a growth inhibitor, FIG. 2D shows a 7-day old culture of *Aspergillus parasiticus* strain B62 illustrating spore production (control). FIG. 2E shows a 7-day old culture of *Aspergillus parasiticus* strain B62 treated with a sporulation inhibitor. Plates with 24 wells were used for these assays.

FIG. 3A-3C illustrate that extracts of *Cladonia cristatella* inhibit secondary metabolite production by *Aspergillus parasiticus* strain B62. FIG. 3A shows a culture of *Cladonia cristatella* mycobiont generated from ascospores. FIG. 3B shows a top view of *Aspergillus parasiticus* strain B62 cultures illustrating that extracts of *Cladonia cristatella* mycobiont grown in liquid or solid culture inhibit secondary metabolite production by *Aspergillus parasiticus* strain B62. FIG. 3B shows a bottom view of *Aspergillus parasiticus* strain B62 cultures illustrating that extracts of *Cladonia cristatella* mycobiont grown in liquid or solid culture inhibit secondary metabolite production by *Aspergillus parasiticus* strain B62. Arrows indicate the orientation of the assay plate such that the top and bottom of the same well is indicated.

FIG. 4A shows an image of *Evernia prunastri*. FIG. 4B illustrates that ethanol extracts of *Evernia prunastri* inhibit growth and aflatoxin accumulation in *Aspergillus* B62 at 3 different concentrations.

FIG. 5A shows TLC separation of *Porpidia* (P) and *Lecidea* (L) extracts collected from an herbarium specimen in 2006. FIG. 5B shows TLC separation of *Porpidia* (P) and *Lecidea* (L) extracts collected from the same herbarium specimen in 2014. As shown, the secondary compounds in stored lichens were stable.

FIG. 7A shows that acetone extracts of lichens *Evernia pruastris* [1] and *Hypogymnia physodes* reduced DON production by cultured *Fusarium graminearum*. FIG. 7B shows that acetone extracts of lichens *Cladonia sylvatica* [15], *Usnea strigosa* [33], *Cladonia digitate* [58], *Ramalina fastigiate* [62], *Ramalina fraxinea* [98], *Platismatia glauca* [100], *Evernia prunastri* [112], and *Cladonia crispata* reduced DON production by cultured *Fusarium graminearum*.

DETAILED DESCRIPTION

Figure 4A:
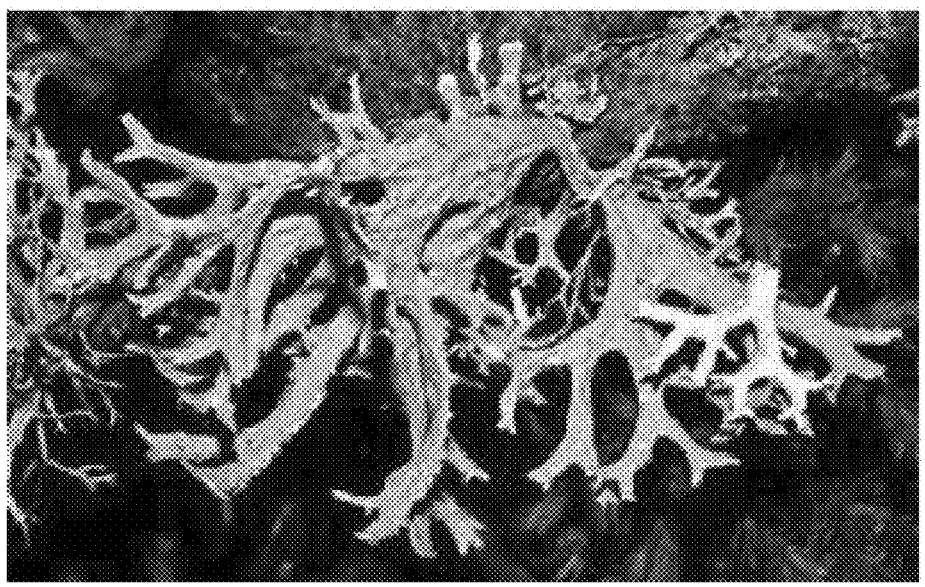
FIG. 4A-4B illustrates that extracts of *Evernia prunastri* strongly inhibit hyphal growth and secondary metabolite production by *Aspergillus parasiticus* strain 1362.

As described herein, lichens can produce a plethora of unique secondary compounds, which are useful in medical, agricultural and food safety applications. Lichens exhibit significant longevity and robustness despite a close association with diverse microbes and harsh environmental conditions. Lichens provide model organisms for identifying and evaluating compounds that can be useful as anti-fungal agents. As described herein, extracts from lichen species were prepared, their activities were tested, and useful compounds have been identified and isolated.

Lichens

Lichens are some of the longest-living organisms known. Despite their slow growth, they very rarely appear die of disease. The lichenized fungus establishes the main lichen thallus in association with an alga or cyanobacterium, and has been recently shown, a basidiomycete yeast is widely included (Spribille et al. Science 3S3: 488-492 (2006)). This scaffold becomes a niche for a variety of other filamentous ascomycetes and basidiomycetes, yeasts, bacteria, and occasionally insects.

Lichens are defined by symbiotic interactions between a fungus and photosynthetic partners, green alga or cyanobacterium. Most species of fungi, including lichenized fungi, produce a plethora of secondary metabolites, which are species-specific nonessential metabolites that are highly diverse and have biological activity. These compounds provide unique functions that can aid organisms in niche-specific adaptations and can serve as defense against disease and predation.

Antibiotics such as penicillin, and cephalosporin are derived from fungi, and fungal derived antifungal griseofulvin is used to treat athlete's foot and toe-nail fungus. Other unique fungal metabolites used in medical applications include: cyclosporins (immunosuppressants), statins (cholesterol lowering drugs) and, fumagillin and pseurotin (angiogenesis inhibitors). One major group of agricultural fungicides, the strobilurins, was originally discovered in extracts of the fungus *Strobilurus tenacellus*.

The methods described herein can provide new types of compounds with useful activities. The inventors can use a unique MSU resource, the Lichen Herbarium, to identify novel compounds to develop into anti-fungal products for medicine and agriculture. The lichen collection in the Plant Biology Department at MSU, an NSF funded herbarium, houses more than 120,000 specimens and has the greatest taxonomic and geographical diversity among its collection compared to all other lichen herbaria in North America.

A variety of types of lichens can be used in the methods described herein and can be a source of useful compounds including, for example, crustose lichens, foliose lichens, leprose lichens, squamulose lichens, and fructose lichens.

Lichens have an algal species associated with a fungal species. Algal species associated with lichens are in the genera *Nostoc*, *Trebouxia* and *Trentephlia*, which comprise the algae in 90% of lichens. These algae can be found free living.

The variation in lichen morphology and physiology is dictated by the fungus. It is therefore most likely that compounds that are uniquely produced by a species of lichen are produced by the fungus.

In some cases, the lichen can include species of the genus *Acarospora, Arctoparmelia, Amandinea, Aspicilia, Austroparmelina, Baeomyces, Biatorina, Buellia, Bryoria, Byssoloma, Calicium, Cladonia, Caloplaca, Candelariella, Cetraria, Cetrelia, Chrysothrix, Cladia, Cladonia, Coenogonium, Collema, Conotrema, Cryptothecia, Dendrographa, Dermatocarpon, Dictyonema, Diploicia, Diploschistes, Dirinaria, Endocarpon, Flavopanctelia, Flavoparmelia, Flavopunctelia, Fulgensia, Fuscopannaria, Graphina, Graphis, Graphis, Gyrophora, Haematomma, Heppia, Herpothallon, Herpothalon, Heterodea, Heterodermia, Hypocenomyce, Hypogymnia, Lasallia, Lecanora, Lecidea, Leioderma, Lepraria, Letharia, Leptogium, Lichen, Lecidea, Lichenomphalia, Lobaria, Menegazzia, Metus, Multiclavula, Myelorrhiza, Neophyllis, Nephroma, Niebla, Nostoc, Ochrolechia, Opegrapha, Opegrapha, Pannaria, Paraparmelia, Paraporpidia, Parmelia, Parmeliella, Parmeliopsis, Parmotrema, Peltigera, Peltigera, Peltula, Pertusaria, Pertusaria, Pertusaria, Pertusaria, Pertusaria, Phaeographina, Phaeophyscia, Phlyctis, Physcia, Physconia, Placidium, Placodium, Placopsis, Placopsis, Platismatia, Pseudephebe, Pseudevernia, Pseudocyphellaria, Pseudocyphellaria, Psora, Punctelia, Pyxine, Ramalina, Ramboldia, Relicina, Rhizocarpon, Rhizoplaca, Roccella, Sagedia, Siphula, Sporopodium, Stereocaulon, Sticta, Stictis, Strigula, Teloschistes, Tephromela, Thamnolia, Thysanothecium, Trapelia, Umbilicaria, Usnea, Xanthomaculina, Xanthopannelia, Xanthoria*, or a combination thereof.

Examples of lichens that can be used include those of the type or species *Acarospora citrina, Arctoparmelia centrifuga, Amandinea punctate, Aspicilia fruticulosa, Aspicilia fruticulosa, Aspicilia vagans, Aspicilia, Austroparmelina pruinata, Austroparmelina pseudorelicina, Baeomyces heteromorphus, Biatorina erysiboides, Bryoria fremontii, Buellia frigida, Buellia foecunda, Buellia grimmiae, Buellia subcoronata, Byssoloma, Calicium chrysocephalum, Caloplaca cinnabarina, Caloplaca cinnabarina, Caloplaca, Candelariella aurella, Cetraria islandica, Cetrelia olivetorum, Chrysothrix xanthine, Chrysothrix, Cladia aggregate, Cladia monilifonnis, Cladia retipora, Cladonia chlorophaceae, Cladonia crispate, Cladonia crispata, Cladonia cristatela, Cladonia didyma, Cladonia digitate, Cladonia fimbriate, Cladonia fimbriate, Cladonia mitis, Cladonia pyxidate, Cladonia pyxidate, Cladonia rangiferina, Cladonia stellaris, Cladonia sylvatica, Cladonia ustulata, Coenogonium implexum, Collema coccophorum, Conotrema urceolatum, Cryptothecia scripta, Dendrographa leucophaea, Dermatocarpon miniatum, Dictyonema sericeum, Diploicia canescens, Diploschistes thunbergianus, Dirinaria pieta, Endocarpon pusillum, Ephebe lanata, Evernia mesomorpha, Evernia prunastri, Flavopanctelia flaventior, Flavopanmelia caperata, Flavopanmelia rutidota, Flavopunctelia soredica, Fulgensia cranfieldii, Fuscopannaria leucosticte, Fuscopannaria leucosticte, Fuscopannaria subimmixta, Graphis bulacana, Graphina rubens, Graphis mucronate, Graphis treubii, Gyrophora murina, Haematomma africanum, Haematomma eremaeum, Heppia despreauxii, Herpothalon rubrocinctum, Heterodea beaugleholei, Heterodea muelleri, Heterodermia leucomelos, Hypocenomyce australis, Hypogymnia physodes, Hypogymnia pulverate, Lasallia papulose, Lasallia pustulata, Lecanora caesiorubella, Lecanora circumborensis, Lecanora conizaeoides, Lecanora epibryon, Lecanora pseudistera, Letharia vulpina, Letharia vulpine, Lecidea terrena, Leioderma pycnophorum, Lepraria lobiflcans, Lepraria lohiticans, Leptogium saturninum, Lichen caninus, Lichen ceuthocarpus, Lichen murorum, Lichen rufescens, Lichen sylvaticus, Lichenomphalia chromacea, Lecidea psora, Lobaria pulmonaria, Menegazzia platytrema, Metus conglomeratus, Multiclavula mucida, Myelorrhiza antrea, Neophyllis melacarpa, Nephroma arctica, Nephroma cellulosum, Niebla cephalota, Nostoc, Ochrolechia tartarea, Opegrapha varia, Opegrapha venosa, Parmelia sulcate, Parmeliella plumbea, Pannaria sphinctrina, Paraparmelia lithophiloides, Paraporpidia leptocarpa, Parmelia signifera, Parmeliopsis chlorolecanorica, Parmotrema perlatum, Peltigera canina, Peltigera trumlata, Peltula euploca, Parmelia sulcate, Pertusaria erebescens, Pertusaria pseudodactylina, Pertusaria subventosa, Pertusaria meleucoides, Pertusaria novaezelandiae, Pertusaria, Phaeographina lamii, Phaeophyscia orbicularis, Phlyctis, Physcia aipolia, Physcia millegrana, Physconia deters, Physcia stellaris, Placidium squamulosum, Placodium murorum, Placopsis perrugosa, Placopsis, Platismatia glauca, Pseudephebe pubescens, Pseudevernia farinacea, Pseudevernia furfuracea, Pseudocyphellaria berberina, Pseudocyphellaria billardierei, Pseudocyphellaria crocata, Pseudocyphellaria freycinetii, Pseudocyphellaria gilva, Pseudocyphellaria norvegica, Pseudocyphellaria multiflda, Pseudocyphellaria gilva, Pseudocyphellaria, Psora crystallifera, Psora decipiens, Punctelia borreri, Punctelia subrudecta, Pyxine cocoes, Ramalina farinacea, Ramalina fastigiate, Ramalina fastigiate, Ramalina fraxinea, Ramalina menziesii, Ramalina siliquosa, Ramalina siliquosa, Caloplaca sp., Tephromela atra, Ramboldia petraeoides, Relicina gemmulosa, Rhizocarpon geographicum, Rhizocarpon geographicum, Rhizoplaca melanophthalma, Roccella canariensis, Roccella portentosa, Sagedia macrospora, Siphula coriacea, Sporopodium vezdeanum, Stereocaulon ramulosum, Stereocaulon saxatile, Sticta limbate, Stictis, Strigula smaragdula, Strigula subtilissima, Teloschistes, Tephromela atra, Thamnolia vermicularis, Thamnolia vermicularis, Thysanothecium scutellatum, Thysanothecium sorediatum, Trapelia crystallifera, Trapelia, Umbilicaria decussata, Umbilicaria hyperborean, Umbilicaria pustulata, Umbilicaria hyperborean, Usnea antarctica, Usnea arizonica, Usnea himantodes, Usnea inermis, Usnea rubicunda, Usnea scabrida, Usnea strigosa, Usnea strigose, Usnea subfloridana, Usnea wasmathii, Xanthomaculina convoluta, Xanthoparmelia amplexula, Xanthoparmelia arapilensis, Xanthoparmelia baeomycesica, Xanthoparmelia chlorochroa, Xanthoparmelia convolute, Xanthoparmelia cravenii, Xanthoparmelia ewersii, Xanthoparmelia mougeotina, Xanthoparmelia notata, Xanthoparmelia praegnans, Xanthoparmelia pseudoamphixantha, Xanthoparmelia pulla, Xanthoparmelia reptans, Xanthoparmelia semiviridis, Xanthoparmelia substrigosa, Xanthoparmelia taractica, Xanthoparmelia versicolor, Xanthoria fllsonii, Xanthoria hasseana, Xanthoria parietina*, or a combination thereof. For example, any of the lichens listed in Appendix I of U.S. Provisional Application Ser. No. 62/702,424, filed Jul. 24, 2018 can be used in the methods described herein and can be a source of useful compounds.

In some cases, lichens such as *Cladonia crispata, Cladonia cristatella, Cladonia digitate, Cetraria islandica, Cetrelia olivetorum, Cladonia sylvatica, Evernia prunastri, Hypogymnia physodes, Platismatia glauca, Pseudevernia furfuracea, Ramalina fastigiate, Ramalina fraxinea, Usnea strigosa,* or a combination thereof can be extracted and/or can be a source of useful compounds.

Mycotoxin

As indicated above, the most serious mycotoxin may be aflatoxin in terms of contamination of crops. Aflatoxin is mainly produced by strains of *Aspergillus flavus* and *Aspergillus parasiticus*, which are ubiquitous in nature. *Aspergillus flavus* and *Aspergillus parasiticus* have no specificity towards their hosts and therefore can infect many different seeds of cereals, nut beans, coffee beans and oil-rich seeds during cultivation, harvest and post-harvest storage. These fungi infect crops such as maize and peanut and produce aflatoxin under the tropical and subtropical environments. Large amounts of aflatoxins can be produced, especially under humid storage conditions.

Deoxynivalenol is the most common trichothecene affecting agriculture production in the US, usually produced by *Fusarium graminearum*, and causing major losses in maize, wheat, barley and other small grains. The presence of rain during grain flowering encourages fungus dispersal and infection. Areas of the Midwest and the Red River Valley are particularly affected by the disease. The presence of the fungus greatly reduces grain yields, and a very small amount of fungal contamination renders barley unusable for malting.

Methods

The activities of lichen extracts were evaluated using experimental fungal organisms to ascertain whether the extracts could inhibit the growth or functions of the fungal organisms. In experiments described herein tested for their effects on sporulation, hyphal growth and mycotoxin production in the filamentous fungus *Aspergillus parasiticus*. For example, *Aspergillus parasiticus* is one of the main producers of aflatoxin.

*Aspergillus parasiticus* is useful for screening for antifungal activity. *A. parasiticus* is a plant pathogen, and produces the mycotoxin aflatoxin. It is extremely closely related to *A. flavus*, a human and plant pathogen, and *A. fumigatus*, a human pathogen. Vegetative growth allows fungi to colonize substrates, such as grain, and human tissues in the case of mycotic disease. Vegetative growth is associated with the production of toxins such as aflatoxin. Sporulation is important in dissemination of fungi in open air, agricultural fields, and in systemic spread through the human body. Small spores are easily carried in the bloodstream. Thus, compounds effective on *A. parasiticus* can be potentially used in medical, agricultural and food safety applications. A primary visual screen of growth, sporulation and secondary metabolism has been performed on lichen extracts using a mutant of *A. parasiticus* called B62 that accumulates norsolorinic acid, an orange-red precursor of aflatoxin (FIG. 2). As illustrated herein, use of this species for assay screens permits quick identification of lichen extract activities.

Also as illustrated herein, *Fusarium graminearum* can be used in assays for screening lichen extracts for inhibiting deoxynivalenol production by the *Fusarium* species.

Lichen extracts can be prepared in a variety of ways. In some embodiments, lichen samples are dried (e.g. at room temperature in the dark). Samples can then be ground in a mill. Samples are then extracted with a solvent (e.g., an alcohol, ethyl acetate, or acetone). Solvents other than alcohols, ethyl acetate, and acetones were not as effective. The solvent employed for extraction can be methanol, ethanol, ethyl acetate, acetone, or a combination thereof.

In some embodiments, extracts are then filtered and dried. The resulting residue can be dissolved in a solvent (e.g., alcohol, ethyl acetate, acetone, water or a combination thereof) to yield a final suspension. In some embodiments, suspensions are generated with different concentrations of lichen material. In some embodiments, the extract preparation methods described in Examples 1-5 below are utilized.

In some embodiments, active ingredients (e.g., with antifungal activity or toxin inhibitory activity) are further purified. Purification methods are well known in the art and include, but are not limited to, extraction, fractionation, and chromatography. The presence of active ingredient is followed at each step of the process (e.g., using the activity assays described herein) and fractions with active ingredients are carried to the next step.

In some embodiments, purified active components are identified. Methods for identifying both small molecule and large molecule (e.g., protein) components are available and include, but are not limited to, high pressure liquid chromatography (HPLC), mass spectroscopy, nuclear magnetic resonance, and combinations thereof.

The experiments described herein illustrate that lichen extracts are useful as inhibitors of fungal growth and fungal functions. For example, several lichen extracts and pure lichen compounds exhibit inhibitory effects on aflatoxin production by *Aspergillus parasiticus*, when grown in culture or on corn kernels, as a model for field conditions. Specifically, pre-treatment of corn kernels with crude extracts of *Cladonia cristatela, Pseudevernia furfuracea, Cetraria islandica, Cetrelia olivetorum*, or *Evernia prunastri* inhibited aflatoxin BI accumulation when applied prior to inoculation with *A. parasiticus*. Extracts of *C. cristatela* showed significant inhibition of AFB I by 99%. Lecanoric acid, identified in the extract of *Cetrelia olivetorum*, and methyl-orsellinate, which is present in *Physcia stellaris* and *Hypogymnia physodes*, demonstrated inhibitory effects on growth and aflatoxin production in *A. parasiticus* culture.

Extracts of 70 lichen species were generated. Three of the seventy extracts inhibited *Aspergillus parasiticus* growth. Ten of the seventy extracts inhibited *Aspergillus parasiticus* sporulation. Fifty-nine of the lichen extracts inhibited secondary metabolite production, where aflatoxin was used as a proxy for secondary metabolite production. The most common activity observed for the lichen extracts across the phylogeny was therefore in arresting secondary metabolite production.

Extracts of two lichens were tested in cultures with *Fusarium graminearum*, using assay methods like those described for *Aspergillus parasiticus*. Treated cultures showed significant reduction in deoxynivalenol and 1-acetyldeoxynivalenol without significant effect on *Fusarium graminearum* growth.

Compositions Compositions described herein can include at least one lichen extract, extract component, or compound purified from a lichen extract. The compositions can also include additional components such as a carrier, solvent, surfactant, an additional active ingredient, or a combination thereof.

These compositions are useful as antibiotics and antifungal compositions.

The composition can contain varying amounts of the extract components, or compounds purified from the extracts described herein. For example, the extracts or compounds can be present in liquid compositions at concentrations of about 0.1 μg/mL to about 1000 μg/mL, or about 1 µg/mL to about 800 µg/mL, or about 3 µg/mL to about 600 µg/mL, or about 5 µg/mL to about 500 µg/mL, or about 5 µg/mL to about 300 µg/mL.

In dry compositions, the extracted components or compounds can be present in at weight/weight concentrations of about 0.1 µg/g to about 1000 µg/g, or about 1 µg/g to about 800 µg/g, or about 3 µg/g to about 600 µg/g, or about 5 µg/g to about 500 µg/g, or about 5 µg/g to about 300 µg/g.

The compositions can therefore be dry compositions or liquid compositions.

In some instances, the extracted components or compounds are dissolved in a solvent to form a liquid composition with a known concentration of at least one component or compound from an extract described herein. The solvent can be an alcohol, ethyl acetate, acetone, water, or a combination thereof. For example, the solvent can be ethanol, methanol, ethyl acetate, acetone, water, or a combination thereof.

The compositions can contain a carrier such as an emulsifier, a dispersing agent, thickening agent, a surfactant, a clay, a polymer, a colorant, a wetting agent of ionic or non-ionic type, a natural or regenerated mineral substance, a dispersant, a wetting agent, a tackifier, a thickener, a binder, or a mixture of such carriers. For example, the compositions can contain polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the present compounds containing sulfate, sulfonate and phosphate functions. The presence of at least one surfactant can be included when the active compound and/or the inert support are water-insoluble and when the vector agent for the application is water. For example, surfactant content can be about 5% to 40% by weight of the composition.

Coloring agents such as inorganic pigments can be present in the composition, for example iron oxide, titanium oxide, ferrocyan blue, and organic pigments such as alizarin, azo and metallophthalocyanine dyes, and trace elements such as iron, manganese, boron, copper, cobalt, molybdenum and zinc salts can be used. The compounds can be present in paints along with any available coloring material(s) and other components typically employed in paints.

Optionally, other additional components may also be included, e.g. protective colloids, adhesives, thickeners, thixotropic agents, penetration agents, stabilizers, sequestering agents.

The compositions can also include other ingredients. For example, bactericidal compounds can be employed. In addition, the compounds described herein can be used together in a composition or they can be used concomitantly with one or more of the other agrichemicals such as various pesticides, acaricides, nematicides, other types of fungicides, and plant growth regulators.

Various types of additional fungicides can optionally be included in the compositions described herein. Examples include copper fungicide such as basic copper chloride and basic copper sulfate, sulfur fungicide such as thiuram, zineb, maneb, mancozeb, ziram, propineb, and polycarbamate, polyhaloalkylthio fungicide such as captan, folpet, dichlorfluanid, organochlorine fungicide such as chlorothalonil, fthalide, organophosphorous fungicide such as O,O-bis(1-methylethyl) S-phenylmethyl phosphorothioate (IBP), edifenphos (EDDP), tolclophos-methyl, pyrazophos, fosetyl, dicarboxylmide fungicide such as iprodione, procymidone, vinclozolin, fluoromide, carboxyamide fungicide such as oxycarboxin, mepronil, flutolanil, tecloftalam, trichlamide, pencycuron, acylalanine fungicide such as metalaxyl, oxadixyl, furalaxyl, methoxyacrylate fungicides such as kresoxim-methyl (stroby), azoxystrobin, metominostrobin, trifloxystrobin, pyraclostrobin, anilinopyrimidine fungicide such as andupurine, mepanipyrim, pyrimethanil, cyprodinil, antibiotic agents such as polyoxin, blasticidin S, kasugamycin, validamycine, dihydrostreptomycin sulfate, propamocarb hydrochloride, quintozene, hydroxyisoxazole, methasulfocarb, anilazine, isoprothiolane, probenazole, chinomethionat, dithianon, dinocap, diclomezine, ferimzone, fluazinam, pyroquilon, tricyclazole, oxolinic acid, iminoctadine acetate, iminoctadine albesilate, cymoxanil, pyrrolnitrin, diethofencarb, binapacryl, lecithin, sodium bicarbonate, fenaminosulf, dodine, dimethomorph, phenazine oxide, carpropamide, flusulfamide, fludioxonil, famoxadone, or combinations thereof. Hence, other types of fungicides can be mixed together with and used in various amounts with one or more of the extracts or compounds described herein.

The extracts, extract components, and compounds described herein can be used in a weight ratio relative to the other type of fungicide such as from 1:0.001 to 1:1000 as a weight ratio. In some instance, the amount of an extract, extract component, or compound purified from a lichen extract relative to the other type of fungicide can vary from 1:0.01 to 1:100 as a weight ratio within a composition.

Pesticides can be included in the compositions, with any of the compounds described herein. The pesticides can include organophosphorous pesticides, carbamate pesticides such as fenthion, fenitrothion, diazinon, chlorpyrifos, ESP, vamidothion, phenthoate, dimethoate, formothion, malathon, trichlorfon, thiometon, phosmet, dichlorvos, acephate, EPBP, methylparathion, oxydemeton-methyl, ethion, salithion, cyanophos, isoxathion, pyridaphenthion, phosalone, methidathion, sulprofos, chlorfevinphos, tetrachlorvinphos, dimethylvinphos, propaphos, isofenphos, ethylthiometon, profenofos, pyraclofos, monocrotophos, azinphosmethyl, aldicarb, methomyl, thiodicarb, carbofuran, carbosulfan, benfuracarb, furathiocarb, propoxur, BPMC, MTMC, MIPC, carbaryl, pirimicarb, ethiofencarb, and fenoxycarb, pyrethroid pesticides such as permethrin, cypermethrin, deltamethrin, fenvalerate, fenpropathrin, pyrethrin, allethrin, tetramethrin, resmethrin, dimethrin, propathrin, phenothrin, prothrin, fluvalinate, cyfluthrin, cyhalothrin, flucythrinate, ethofenprox, cycloprothrin, tralomethrin, silafluofen, brofenprox, and acrinathrin, and benzoylurea and other types of pesticides such as diflubenzuron, chlorfluazuron, hexaflumuron, triflumuron, tetrabenzuron, flufenoxuron, flucycloxuron, buprofezin, pyriproxyfen, methoprene, benzoepin, diafenthiuron, acetamiprid, imidacloprid, nitenpyram, fipronil, cartap, thiocyclam, bensultap, nicotin sulfate, rotenone, mataldehyde, machine oil, and microbial pesticides e.g. BT and insect pathogenic virus.

Acricides can be included in the compositions described herein. The acricides that can be employed include, for example, chlorbenzilate, phenisobromolate, dicofol, amitraz, BPPS, benzomate, hexythiazox, fenbutatin oxide, polynactin, chinomethionat, CPCBS, tetradifon, avermectin, milbemectin, clofentezin, cyhexatin, pyridaben, fenpyroximate, tebufenpyrad, pylidimifen, fenothiocarb, and dienochlor.

As for the aforementioned nematicides, fenamiphos, fosthiazate and the like can be specifically exemplified; as for plant-growth regulators, gibberellins (e.g., gibberellin A3, gibberellin A4, and gibberellin A7), auxin, 1-naphthaleneacetic acid, and so on can be specifically exemplified.

More generally, the active compounds can be combined with any solid or liquid additive, which complies with the usual formulation techniques. In general, the composition according to the invention may contain from 0.05 to 99% by weight of active compounds, preferably from 10 to 70% by weight.

The extracts, extract component, extracted compounds or compositions can be provided in a form that is ready-to-use or in a form that can be prepared for use. The extracts, extract component, extracted compounds, or compositions can be applied by a suitable device, such by use of a spraying or dusting device. The extracts, extract component, extracted compounds, or compositions can be applied by use of brush or roller.

The extracts, extract component, extracted compounds, or compositions can be provided in concentrated commercial compositions that should be diluted before application to the crop. For example, the extracts, extract component, extracted compounds, or compositions can be provided in dry (e.g., lyophilized) form, or in concentrated form, and then dissolved or diluted as desired. The compositions can be in formulated into an aerosol dispenser, as a capsule suspension, as a cold fogging concentrate, as a dustable powder, as an emulsifiable concentrate, as an emulsion oil in water, as an emulsion water in oil, as an encapsulated granule, as a fine granule, as a flowable concentrate for seed or nut treatment, as a gas (under pressure), as a gas generating product, as granules, as a hot fogging concentrate, as macrogranules, as microgranules, as an oil dispersible powder, as an oil miscible flowable concentrate, as an oil miscible liquid, as a paste, as a plant rodlet, as a powder for dry seed or nut treatment, as seeds or nuts coated with the composition, as a soluble concentrate, as a soluble powder, as a solution for seed (or other) treatment, as a suspension concentrate (flowable concentrate), as an ultra-low volume (ULV) liquid, as an ultra-low volume (ULV) suspension, as water dispersible granules or tablets, as a water dispersible powder for slurry treatment, as water soluble granules or tablets, as a water soluble powder for seed or nut treatment, as a wettable powder, or as a combination thereof (e.g., two types of formulations packaged together).

The following Examples illustrate some of the experimental work involved in the development of the invention.

Example 1: Materials and Methods

This Example describes materials and methods for extraction of lichens. Lichens were collected fresh, and in some cases herbarium specimens were surveyed, where the oldest herbarium specimen dated back to 1949. Extracts were done in methanol, ethanol, ethyl acetate, and acetone; other solvents did not appear to extract activities as well. Activities were found to be quite stable in herbarium specimens, even amongst the oldest specimens.

A primary visual screen of growth, sporulation and secondary metabolism was performed on lichen extracts using a mutant of *Aspergillus parasiticus* strain B62 which accumulates norsolorinic acid (NA), an orange-red precursor of aflatoxin. Norsolorinic acid quantification was performed by use of a chromameter. Use of this species for initial screens has facilitated fast identification of activities.

Extracts of two lichens were tested in cultures with *Fusarium graminearum*, using methods like the assay methods used for *Aspergillus parasiticus*. *Aspergillus parasiticus* was grown on glucose mineral salts (GMS) medium. *Fusarium graminearum* was grown on High DON Medium from Linda Harris (McCormick et al., *Appl. Environ. Microbiol.* 70:2044-2051 (2004)).

Example 2: *Aspergillus parasiticus* Strain B62 Treated with Lichen Extracts

A set of high-throughput screens for discovery of antifungal agents were developed using spices as a potential source of inhibitors of mycotoxin biosynthesis. Black pepper extracts were used in an initial screen.

Extracts of spices were added to *Aspergillus parasiticus* B62 cultures in GMS, YES, and PMS media (Buchanan & Lewis (1984)) as described in Annis et al. (2000). Changes in growth, sporulation and mycotoxin production were observed. Extracts with promising effects were screened using the Thin Layer Chromatography (TLC) bioassay developed by the inventors and coworkers (Annis et al., 2000; Trail et al. 2006). This technique resulted in the identification of a novel activity in black pepper that turned off genes for aflatoxin production but did not arrest fungal growth. Based on HPLC, and MS analysis, putative structures were synthesized and two active structures have been identified. One structure inhibits aflatoxin biosynthesis but does not affect fungal growth, the other inhibits fungal growth.

In preliminary studies, extracts from four lichen species were tested for effects on growth, sporulation and mycotoxin biosynthesis in *A. parasiticus* (FIG. 2). Extracts from one lichen species inhibited fungal growth, and extracts from a second lichen greatly reduced aflatoxin accumulation, but did not affect growth, and inhibited sporulation. These preliminary trials indicate a high frequency of bioactive compounds in a small group of randomly selected lichens.

High through-put assays were performed in 24 well plates to evaluate the antifungal effects of lichen extracts on the fungal *Aspergillus parasiticus* strain B62. An orange-red pigment was a precursor and indicator of aflatoxin production.

FIG. 2A-2E illustrate high through-put assays in 24 well plates for antifungal effects of lichen extracts on the fungus *Aspergillus parasiticus* strain B62. FIG. 2A shows a 3-day old culture of *Aspergillus parasiticus* strain B62 that was not treated (control). FIG. 2B shows a 3-day old culture of *Aspergillus parasiticus* strain B62 treated with an aflatoxin biosynthesis inhibitor. FIG. 2C shows a 3-day old culture of *Aspergillus parasiticus* strain B62 treated with a growth inhibitor, FIG. 2D shows a 7-day old culture of *Aspergillus parasiticus* strain B62 illustrating spore production (control). FIG. 2E shows a 7-day old culture of *Aspergillus parasiticus* strain B62 treated with a sporulation inhibitor. Plates with 24 wells were used for these assays.

Example 3: Assay Results

Table 1 shows results of assays for inhibition of growth, aflatoxin production, and sporulation of *Aspergillus parasiticus* B62 by extracts of the indicated lichen species are shown. The growth, aflatoxin production, and sporulation of *Aspergillus parasiticus* B62 was compared to Control. The symbols used in Table 1 were: N—No effect; SI—Strong Inhibition (90-100%); I—Inhibition (38-80%); A—Activation (~150%); SA—Strong Activation (>150%).

TABLE 1

Effects of Lichen Extracts on growth, aflatoxin production, and sporulation of *Aspergillus parasiticus* B62

| Lichen species | Growth | Aflatoxin | Sporulation |
|---|---|---|---|
| *Bryoria fremontii* | N | SI | N |
| *Cetraria islandica* | N | SI | N |
| Latvia May 2016 | (I Fract) | | |
| *Cetrelia olivetorum* | | | |
| CA Bay Area August 2016 | | | |
| *Cetrelia* sp CA Bay Area | | | |
| August 2016 | | | |
| *Cladonia chlorophaceae* | N | I | N |
| Pellston MI 3 Oct. 2015 | | | |
| *Cladonia crispata* | | | |
| Pellstone MI 17 Sep. 2016 | | | |
| *Cladonia cristatela* (British soldier) | N | SI | N |
| Frances 17 Nov. 2015 | | | |
| Red Caps/Rotten Cart | | | |
| *Cladonia didyma* + | N | SI | A |
| *Cladonia fimbriata* | | | |
| *Cladonia digitata* | N | SI | N |
| Latvia, Lielupe, 9 Aug. 2015 | | | |
| *Cladonia mitis* | | | |
| Pellstone MI | | | |
| 17 Sep. 2016 | | | |
| *Cladonia pyxidata* (Owen) | N | I | N |
| *Cladonia rangiferina* | N | I | A |
| Latvia May 2016 Ropazi | | | |
| Maris Small | | | |
| quantity | | | |
| *Cladonia stellaris* | N | SI | I |
| Yoshkar-Ola 2009 | | | |
| *Cladonia sylvatica* | I | SI | I |
| Yoshkar-Ola 2009 | | | |
| *Dendrographa leucophaea* | N | SI | N |
| f. minor Frances March CA 2017 | | | |
| *Dermatocarpon miniatum* | N | SI | N |
| S Dakota Black Hills on | | | |
| rock Herbarium | | | |
| *Ephebe lanata* | N | SI | N |
| Flora Suecica 1961 Herbarium | | | |
| *Evernia mesomorpha* | N | SI | N |
| Pellston (#3) 3 Oct. 2015 | | | |
| *Evernia prunastri* | SI | SI | SI |
| Yoshkar-Ola 2009/GB 2015 | | | |
| *Flavopanctelia flaventior* | N | SI | I |
| by Green House 19 Jun. 2015 | | | |
| *Flavoparmelia caperata* | N | SI | I |
| by Green House 19 Jun. 2015 | | | |
| *Flavopunctelia soredica* | N | SI | N |
| Quercus alba tree, F.T., 8 Aug. 15 | | | |
| *Fuscopannaria leucosticta* | N | N | N |
| N Carolina 1967 Herbarium | | | |
| *Graphis bulacana* | N | SI | N |
| West Indies Trinidad | | | |
| 1963 Herbarium | | | |
| *Herpothalon rubrocinctum* 2016 | | | |
| *Hypogymnia physodes* | I | SI | SI |
| Latvia, Lielupe, 9 Aug. 2015 | | | |
| *Lecanora caesiorubella* | | | |
| CA March 2017 | | | |
| *Lecanora circumborensis* | | | |
| CA March 2017 | | | |
| *Lecidea psora* | N | SI | |
| Wyoming 1956 Herbarium | | | |
| *Lepraria lohiticans* | | | N |
| "Amorphic" Dust Lichen | | | |
| Pellston MI 3 Oct. 2015 | | | |
| *Leptogium saturninum* | N | I | |
| S Dakota Alan 1961 | | | |
| *Letharia vulpina*, | N | SI | N |
| wolf lichen, Alan, 1994 | | | |
| *Lobaria pulmonaria* | | | N |
| Maine Frances 10-15 Jul. 2016 | | | |
| *Nephroma arctica* | N | SI | |
| MSC0066318 | | | |
| *Niebla cephalota* | N | SI | N |
| Asilomar 2015 | | | |
| *Parmelia sulcata* + | N | SI | N |
| *Flavoparmelia caperata* | | | |
| *Parmeliella plumbea* | N | SI | N |
| Canary Islands Tenerife | | | |
| 1964 Herbarium | | | |
| *Peltigera canina* | N | I/N | N |
| Pellston MI 3 Oct. 2015, (#10) | | | |
| *Peltigera trumlata* AF10981 | N | I | N |
| *Peltula euploca* | N | SI | A |
| Colorado Rabit Mt | | | |
| 1960 Herbarium | | | |
| *Pertusaria erebescens* | N | N | N |
| East Falklands Kidney Isl, | | | |
| 1968 Herbarium | | | |
| *Phaeophyscia orbicularis*, Alan | N | I | N |
| *Physcia aipolia* Memos 2014 | N | SI | N |
| *Physcia millegrana* | N | SI | SA |
| Frances' Yard 22 Jun. 2015 | | | |
| *Physcia stellaris* | N | SI | I |
| by Vet Clinic 19 Nov. 2015 | | | |
| *Physconia deters* | N | I | I |
| MI Alan 8 Oct. 1976 | | | |
| *Platismania glauca* | N | SI | I |
| Latvia May 2016 Ropazi Maris/Ilze | | | |
| *Pseudevernia farinacea* | N(I/SI Fracts) | SI | N |
| Latvia May 2016 Ropazi Maris/Ilze | | | |
| (*P. furfuracea* by ITS/NCBI) | | | |
| *Pseudevernia furfuracea* | I | SI | N |
| Latvia, Lielupe, 9 Aug. 2015 | | | |
| *Pseudocyphellaria berberina* | N | N | SI |
| AF10717 | | | |
| *Pseudocyphellaria crocata* | N | SI | N |
| AF10876 | | | |
| *Pseudocyphellaria freycinetii* | N | SI | I(?) |
| AF 10716 | | | |
| *Psendocyphellaria gilva*, AF 10877 | N | SI | N |
| *Pseudocyphellaria norvegica* | N | I | N |
| AF10878 | | | |
| *Ramalina farinacea* | N | N | N |
| Asilomar March 2015 | | | |
| *Romalina fastigiata* | N | SI | N |
| Latvia, Lielupe, 9 Aug. 2015 | | | |
| *Ramalina fraxinea* Latvia May 2016 | N | I | I |
| Carnicava Skaidrite | | | |
| *Romalina menziesii* Asilomar 2015 | N | SI | A(one well) |
| *Rhizoplaca melanophthalma* | N | N | N |
| S Dakota Black Hills | | | |
| 1960 Herbarium | | | |
| *Roccella portentosa* | N | SI | N |
| Chile Alan 14 Nov. 1965 | | | |
| *Stereocaulon saxatile* | N | SI | N |
| MI Cheboygan | | | |
| County 1949 Herbarium | | | |
| *Thamnolia vermicularis* | N | SI | N |
| British Columbia 1970 Herbarium | | | |
| *Umbilicaria hyperborea* + | N | I | N |
| *Pseudephebe* | | | |
| *pubescens* | | | |
| *Usnea arizonica* | | | |
| Maine July 2016 Frances | | | |
| *Usnea rubicunda* | N | N | N |
| Asilomar March 2015 | | | |
| *Usnea strigosa* | N | I | N |
| *Usnea subfloridana* | N | SI | N |
| *Usnea wasmathii* | | | SI |
| Latvia May 2016 | | | |
| Ropazi Maris/Ilze Small quantity | | | |
| *Xanthoparmelia chlorochroa* | A | SI | |
| *Xanthoria hasseana* | N | I | SA |
| yellow Pellston (#3) | | | |
| 3 Oct. 2015 | | | |
| *Xanthoria parietina* | N | SI | N? |

Example 4: *Cladonia cristatella* Extracts Inhibit Secondary Metabolite Production This Example illustrates that extracts of *Cladonia cristatella* inhibits secondary metabolite production by *Aspergillus parasiticus* strain B62.

Ascospores from *Cladonia cristatella* were isolated and cultured as illustrated in FIG. 3A. Colonies from these colonies were extracted with ethanol and acetone. *Aspergillus parasiticus* strain B62 was cultured with the extracts. As illustrated in FIG. 3B, the extracts inhibited secondary metabolite production by *Aspergillus parasiticus* strain B62.

Example 5: *Evernia prunastri* Extracts Inhibit Hyphal Growth, Secondary Metabolite Production, and Sporulation This Example illustrates that extracts of *Evernia prunastri* inhibit hyphal growth, secondary metabolite production, and sporulation by *Aspergillus parasiticus* strain B62.

Figure 4B:
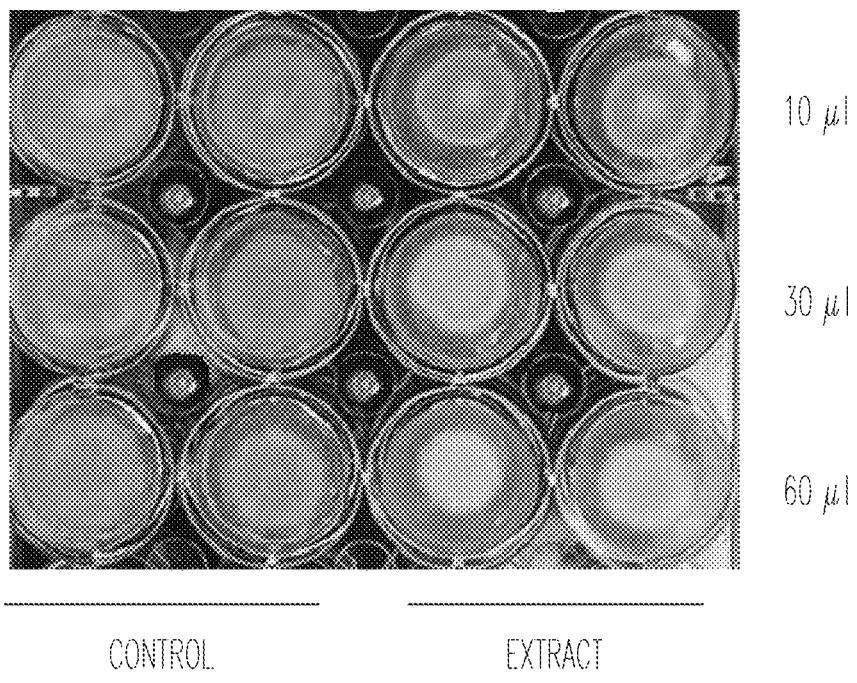
Figure 5A:
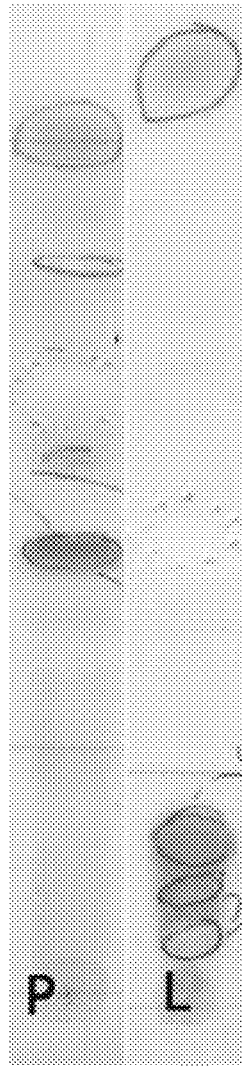
FIG. 5A-5B illustrates of the stability of secondary metabolites of lichen species *Porpidia* (P) and *Lecidea* (L) as shown by thin layer chromatography (TLC).
Figure 5B:
Figure 6:
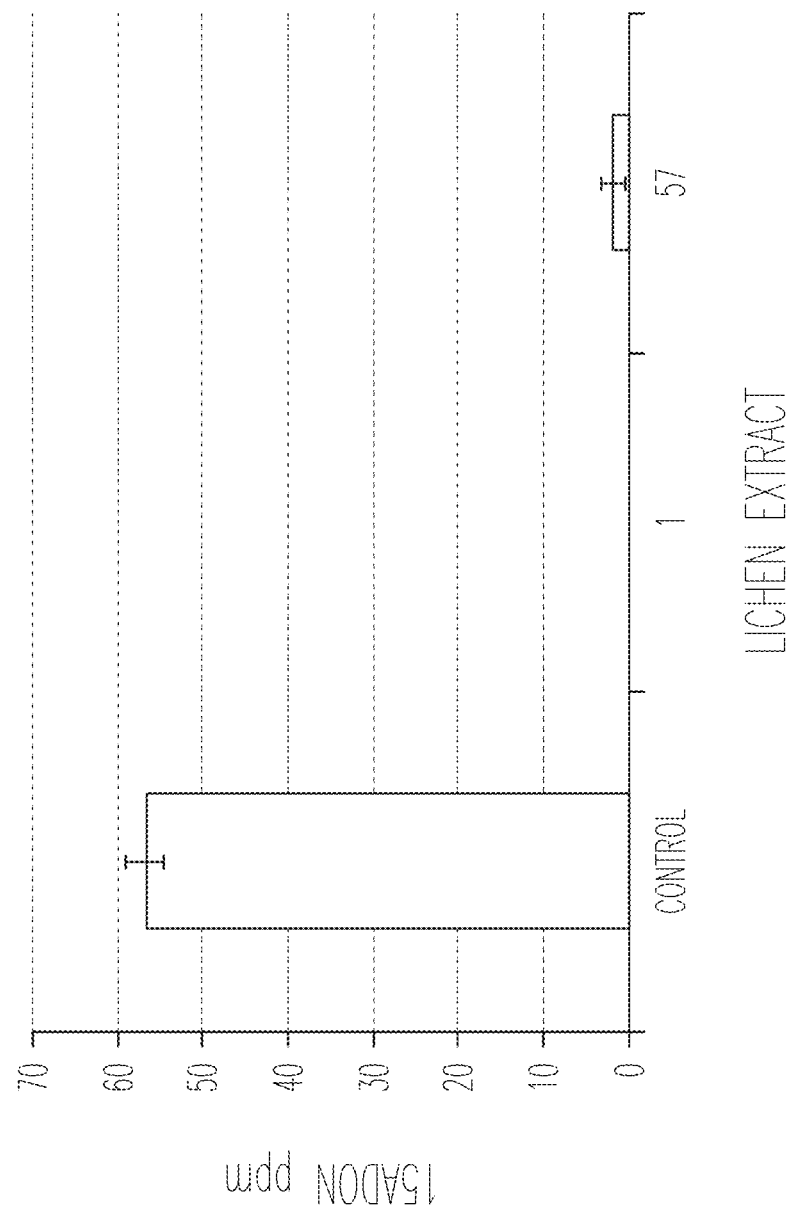
FIG. 6 illustrates that extracts of two lichens (*Evernia pruastris* [1], and *Hypogymnia physodes* [57]) whose extracts reduced 15-acetyl-deoxynivalenol (15-ADON) accumulation in the assay described for FIG. 2 in comparison with cultures that were treated with equivalent amounts of solvent (ethanol or acetone).
Figure 7A:
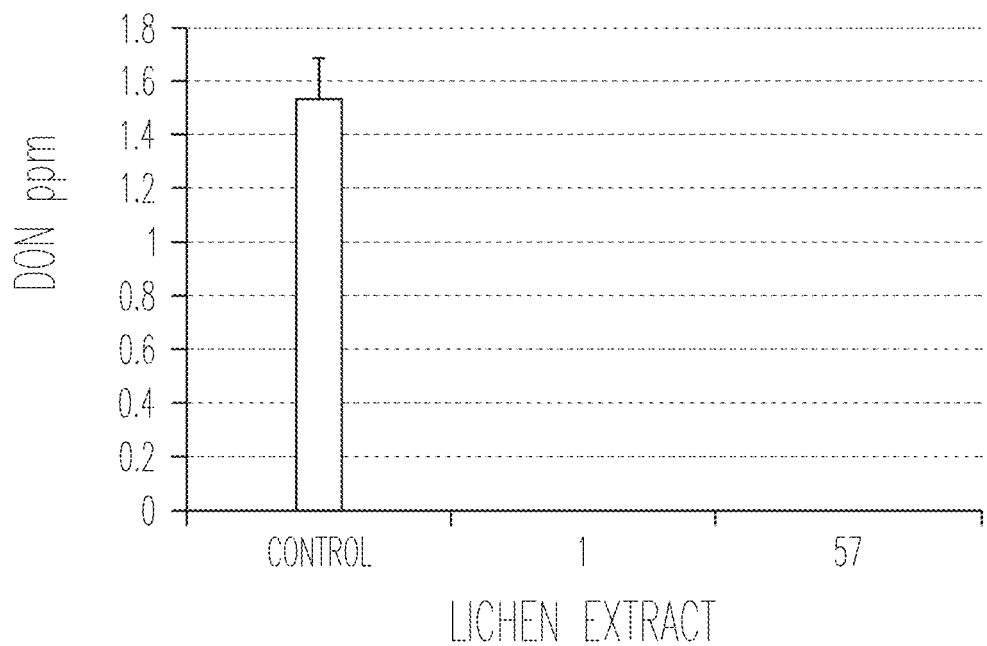
FIG. 7A-7B illustrate that lichen extracts inhibit deoxynivalenol (DON) accumulation by *Fusarium graminearum*.
Figure 7B:
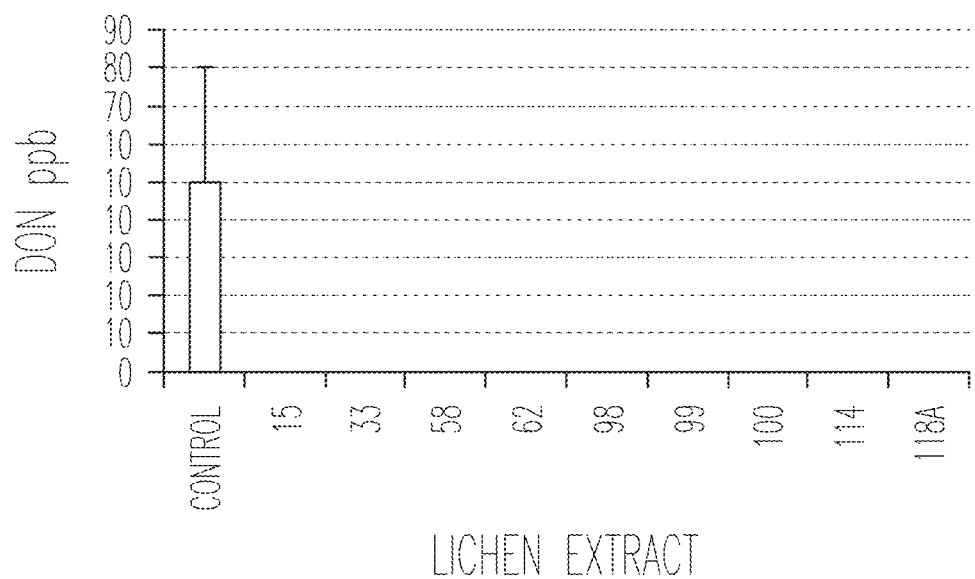

Extracts of *Evernia prunastri* were cultured with *Aspergillus parasiticus* B62 in GMS (Buchanan & Lewis, 1984). As illustrated in FIG. 4B the *Evernia prunastri* extracts exhibited strong inhibitory activity against hyphal growth, secondary metabolite production and sporulation by *Aspergillus parasiticus* B62. Purification of the active compound and X-ray crystallography determined that evernic acid was present in active fraction of *Evernia prunastri* extracts, where the evernic acid structure is shown below.

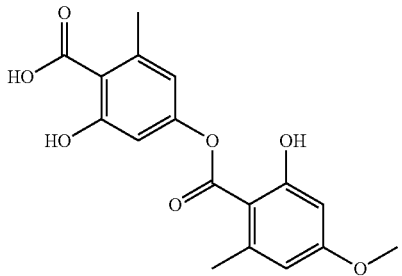 [SMILES: COc1cc(C)c(C(=O)Oc2cc(C)c(C(=O)O)c(O)c2)c(O)c1]

Example 6: Lichen Extracts Inhibit Accumulation of Aflatoxins in Corn Kernels The following lichen extracts were tested for their capacity to reduce aflatoxin accumulation in corn kernels.
1 *Evernia prunastri*

81 *Cladonia cristatella*

99 *Pseudevernia farinacea*

101 *Cetraria islandica*

129 *Dendrographa leucophaea* f. minor

Extracts of lichens #1, 99 and 101 demonstrated protective effects against aflatoxin contamination, showing 80-70% inhibition of aflatoxin accumulation on DeDell field corn kernels (200 spores/kernel, 96 h post inoculation). Extracts obtained from lichen #81 inhibited aflatoxin B1 accumulation by 99% on sweet corn kernels. The extract from #129 was active on Monsanto field corn kernels after 72 h post inoculation. All of these represent statistically significant findings.

Example 7: Stability of Compounds in Lichen Material During Storage and Use of Herbarium Specimens for Extraction Chemicals preserved in dry lichens appear to be largely stable under standard herbarium storage conditions. Thin layer chromatography (TLC) analyses of acetone extracts from the identical lichen specimens obtained eight years apart demonstrated similar metabolite profiles (FIG. 5A-5B).

Example 8: Lichen Extracts Reduce 1-Acetyldeoxynivalenol by *Fusarium graminearum*

Extracts of two lichens, *Evernia pruastris and Hypogymnia physodes*, were tested in cultures with *Fusarium graminearum*, using assay methods like those used for the assays of *Aspergillus parasiticus.*

As illustrated in FIG. 6, the *Fusarium graminearum* cultures treated with these lichen extracts (*Evernia pruastris* [number 1], and *Hypogymnia physodes* [number 57]) showed significant reduction in 1-acetyldeoxynivalenol production without significant effects on growth.

Example 9: Extracts of Various Lichen Reduce Deoxynivalenol Production

The fungus *Fusarium graminearum* is a plant pathogen which causes fusarium head blight, a devastating disease on wheat and barley. This Example illustrates that extracts from various lichens can reduce deoxynivalenol (DON) production by *Fusarium graminearum.*

In a first experiment, *Fusarium graminearum* cultures were grown in 24-well plates for 6 days in the dark at room temperature. Each well contained 1 ml High DON Medium (McCormick et al., 2004) plus 20 μl of lichen extract (either *Evernia pruastris* [number 1] or *Hypogymnia physodes* [number 57]), while control wells contained 20 μl ethanol without a lichen extract. Cultures exhibiting decreased production of red/pink pigment but no effects on growth were analyzed for DON accumulation. FIG. 7A shows the effects of these lichen ethanol extracts on DON accumulation by *Fusarium graminearum* grown in culture for 6 days.

In a second experiment, *Fusarium graminearum* cultures were grown in 24-well plates for 6 days in the dark at room temperature. Each well contained 1 ml High DON Medium plus 20 μl of a lichen extract from *Cladonia sylvatica* [15], *Usnea strigosa* [33], *Cladonia digitate* [58], *Ramalina fastigiate* [62], *Ramalina fraxinea* [98], *Platismatica glauca* [100], *Evernia prunastri* [112], or *Cladonia crispata* [118]. Control wells contained 20 μl acetone without any lichen extract. Cultures exhibiting decreased production of red/pink pigment but no effects on growth were analyzed for DON accumulation.

As shown in FIG. 7B acetone extracts of lichen extracts from *Cladonia sylvatica* [15], *Usnea strigosa* [33], *Cladonia digitate* [58], *Ramalina fastigiate* [62], *Ramalina fraxinea* [98], *Platismatia glauca* [100], *Evernia prunasiti* [112], and *Cladonia crispata* [118] all reduced DON production by *Fusarium graminearum.*

Example 10: Extracts of Various Lichen Remain Stable for Decades

This Example described results of assaying various lichens that had been stored for extended periods of time to determine if they could still inhibit growth, norsolorinic acid (NA) production, and sporulation by *Aspergillus parasiticus.*

Lichens were obtained after storage under herbarium storage conditions, extracts were made, and the extracts were added to *Aspergillus parasiticus* cultures. This assessment of lichen extract activity was performed in 2014-2015.

Table 2 shows which lichens were evaluated, and whether the *Aspergillus parasiticus* grew, accumulated norsolorinic acid, and sporulated (N indicates that no growth, no NA, or no sporulation was observed).

TABLE 2

Activity of lichen compounds to inhibit Norsolorinic Acid accumulation is stable for decades under Herbarium storage conditions.

| ID number | Lichen/ Year collected/ Storage facility | Growth | Inhibition of Norsolorinic acid accumulation | Sporulation |
|---|---|---|---|---|
| 85 | *Stereolaulon saxatile*, Michigan Cheboygan County 1949, MSU Herbarium | N | 90-100% | N |
| 87 | *Petula euploca*, Colorado Rabbit Mt, 1960, MSU Herbarium | N | 90-100% | N |
| 88 | *Graphis bulacana*, West Indies, Trinidad, 1963, MSU Herbarium | N | 90-100% | N |
| 90 | *Ephebe lanata*, Flora Suecica, 1961, MSU Herbarium | N | 90-100% | N |
| 93 | *Lecidea psora*, Wyoming, 1956, MSU Herbarium | N | 90-100% | N |

Activity of assay was performed in 2014-2015. N, no effect.

As illustrated, each of the lichens shown in Table 2 inhibited 90-100% of norsolorinic acid accumulation even though the lichens had been stored since 1949-1963.

REFERENCES

Annis S L, Velasquez L, Xu H, Hammerschmidt R, Linz J, Trail F. 2000. *J Agric Food Chem.* 48(10):4656-60.

Buchanan R L and Lewis D F, *Appl. Environ Microbiol.* 48(2):306-10 (1984).

Butler M S, Fontaine F, and Cooper M A. 2013. *Planta Med.* Epub ahead of print. Georg Thieme Verlag K G Stuttgart, New York.

Cheon, D M, Jang D S, Kim H Y, Choi K S, Choi S K. 2013. *Korean J. Microbiol. Biotechnol.* 49(2): 165-171.

Fisher M C, Henk D A, Briggs C J, Brownstein J S, Madoff L C, McCraw S L, Gurr S J. 2012. *Nature* 484:186-194.

Gaffoor I, Brown D W, Plattner R, Proctor R H, Qi W, Trail F. 2005. *Euk Cell.* 4:1926-1933

Gao L, Cai M, Shen W, Xiao S, Zhou X and Y Zhang. 2013. *Microbial Cell Factories* 2013, 12:77.

Kim E S, Kap S C, and Sang K C. 2012. *Korean J. Microbiol. Biotechnol.* 40 (1): 23-29.

Kupferschmidt K. 2012. *Science* 337:636-638.

Magan N, Medina A, Aldred D. 2011. *Plant Pathology* 60:150-163.

Miao V, Coeffet-LeGal M-F, Brown D, Sinnemann S, Donaldson G, Davies J. 2001. *TRENDS in Biotechnology* 19(9): 349-355.

Mitrović T, Stamenković S, Cvetković V, Toke S, Stanković M, Radojević I, Stefanović O, Čomić L, Ðačić D, Curčić M, and Marković S. 2011. *Int. J. Mol. Sci.* 12, 5428-5448.

Roze L V, Beaudry R M, Arthur A E, Calvo A M, and J E Linz. 2007. *Appl Environ Microbiol.* 73(22): 7268-7276.

Roze L V, Koptina A V, Laivenieks M, Beaudry R M, Jones D A, Kanarsky A V, Linz J E. 2011. *Appl Microbiol Biotechnol.* 92(2):359-70.

Rugbjerg P, Naesb M, Uffe H Mortensen U H, and Frandsen R J N. *Microbial Cell Factories* 2013, 12:31

Shrestha G, and St. Clair L L. 2013. *Phytochem Rev* 12:229-244.

Trail F, Hammerschmidt R, Linz J E, Xu, H, Velasquez L, Annis S. 2004. U.S. Pat. No. 6,825,216.

Trail F, Hammerschmidt R, Linz J E, Xu, H, Velasquez L, Annis S. 2006. U.S. Pat. No. 7,041,678.

Zambare V P and Christopher L P. 2012. *Pharmaceutical Biology* 50(6): 778-798.

Wiemann P, and Keller N P. 2013. *J Ind Microbiol Biotechnol.* Epub ahead of print.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements describe some of the elements or features of the invention. Because this application is a provisional application, these statements may become changed upon preparation and filing of a nonprovisional application. Such changes are not intended to affect the scope of equivalents according to the claims issuing from the nonprovisional application, if such changes occur. According to 35 U.S.C. § 111(b), claims are not required for a provisional application. Consequently, the statements of the invention cannot be interpreted to be claims pursuant to 35 U.S.C. § 112.

Statements:

1. A method comprising extracting a lichen sample with alcohol, ethyl acetate, acetone or a combination thereof to provide a lichen extract, and measuring whether the lichen extract inhibits the growth, sporulation, or mycotoxin production of a fungus.
2. The method of statement 1, wherein the fungus produces aflatoxin.
3. The method of statement 1 or 2, wherein the fungus is an *Aspergillus* or a *Fusarium*.
4. The method of statement 1, 2, or 3, wherein the fungus is an *Aspergillus parasiticus*.
5. The method of statement 1-3 or 4, wherein the fungus is *Aspergillus parasiticus* strain B62.
6. The method of statement 1-4 or 5, wherein the fungus is *Fusarium graminearum*.
7. The method of statement 1-5 or 6, wherein the alcohol is methanol or ethanol.
8. The method of statement 1-5 or 6, wherein the lichen sample is extracted with acetone.
9. The method of statement 1-7 or 8, further comprising purification of a compound that inhibits the growth, sporulation, or mycotoxin production of a fungus from the lichen extract to provide a purified compound.
10. The method of statement 1-8 or 9, further comprising determining a structure of a compound that inhibits the growth, sporulation, or mycotoxin production of a fungus from the lichen extract to provide a compound with a structure.
11. The method of statement 1-9 or 10, further comprising determining an amount of the purified compound or the compound with the structure that inhibits the growth, sporulation, or mycotoxin production of a fungus.

12. The method of statement 1-10 or 11, further comprising applying the lichen extract, the purified compound, or the compound with the structure to a surface, an agricultural crop, a storage bin, a storage facility, an animal feed, a plant seed, a nut, a plant part, a plant product, or a combination thereof.
13. The method of statement 1-11 or 12, wherein the surface is a bathroom, a kitchen, a Closet, a basement, an attic, an entryway, a cabinet, a boat, a barn, an animal shelter, a warehouse, a grain storage compartment, or a food storage facility surface.
14. The method of statement 1-12 or 13, wherein the plants comprise grain-producing plants, nut-producing plants, vegetable-producing plants, fruit-producing plants, starch-producing plants, fiber-producing plants, fodder-producing plants, grains, nuts, vegetables, fruits, starch, fibers, flour, fodder, leaves, stock, seeds, oil, or a combination thereof.
15. The method of statement 1-13 or 14, wherein the plant products are almonds, barley, betel nuts, brazil nuts, cashews, chestnuts, coconut, coffee, corn, flour, hazelnuts, macadamia nuts, oats, pecans, peanuts, pine nuts, pistachios, rice, rye, sesame seeds, soybean, spices, walnuts, wheat, or combinations thereof.
16. The method of statement 1-14 or 15, wherein the mycotoxin content in a surface, an agricultural crop, a storage bin, a storage facility, an animal feed, a plant seed, a nut, a plant part, a plant product, or a combination thereof is reduced by spraying a composition onto the plants or plant products.
17. The method of statement 1-14 or 15, wherein the mycotoxin content is reduced by at least 10%, at least 20%, at least 30%, at least 40%, at least 50%, at least 60%, at least 70%, at least 80%, at least 90%, at least 95%, or at least 99%.
18. The method of statement 1-16 or 17, wherein the lichen is any of the lichens described in this application.
19. The method of statement 1-17 or 18, wherein the lichen is *Cladonia crispata, Cladonia cristatella, Cladonia digitate, Cetraria islandica, Cetrelia olivetorum, Cladonia sylvatica, Evernia prunastri, Hypogymnia physodes, Platismatia glauca, Pseudevernia furfuracea, Ramalina fastigiate, Ramalina fraxinea, Usnea strigosa*, or a combination thereof
20. An extract obtained by the method of statement 1-18 or 19.
21. An extract component or compound Obtained by the method of statement 1-19 or 20.
22. An extract comprising lichen compounds solubilized in alcohol, ethyl acetate, acetone or a combination thereof.
23. A composition comprising a carrier and an extract, compound, or a component of an extract obtained by the method of statement 1-18 or 19.
24. The composition of statement 23, where the carrier is a solvent or surfactant.
25. The composition of statement 23 or 24, where the carrier is a solvent selected from methanol, ethanol, ethyl acetate, or acetone.
26. The composition of statement 23-24 or 25, where the carrier is an emulsifier, a dispersing agent, a thickening agent, a surfactant, a clay, a polymer, a colorant, a wetting agent, a mineral substance, a dispersant, a tackifier, a thickener, a binder, or a mixture of such carriers.
27. The composition of statement 23-25 or 26, wherein the compound(s) are at a concentration of 0.1 μg/mL to about 1000 μg/mL, or about 1 μg/mL to about 800 μg/mL, or about 3 μg/mL to about 600 μg/mL, or about 5 μg/mL to about 500 μg/mL, or about 5 μg/mL to about 300 μg/mL.
28. The composition of statement 23-26 or 27, wherein the composition comprises weight/weight concentrations of one or more compounds at about 0.1 μg/g to about 1000 μg/g, or about 1 μg/g to about 800 μg/g, or about 3 μg/g to about 600 μg/g, or about 5 μg/g to about 500 μg/g, or about 5 μg/g to about 300 μg/g.
29. The composition of statement 23-27 or 28, wherein the compound(s) are at a concentration of about 0.1 ppm to 500 ppm, or about 1 ppm to 400 ppm, or about 2 ppm to 300 ppm, or about 5 ppm to 250 ppm, or about 10 ppm to 150 ppm, or about 12 ppm to 100 ppm, or about 15 to 50 ppm, or about 20 ppm to 35 ppm, or about 25 ppm.

What is claimed:

1. A method comprising applying a composition comprising a carrier and evernic acid, methyl orsellinate, or a combination thereof to a structure, to a surface, to a storage bin, to a storage facility, to grain, or a combination thereof to thereby reduce or prevent mycotoxin production, mycotoxin contamination, or both, of the grain or grain stored on or in the surface, the storage bin, or the storage facility.
2. The method of claim 1, wherein the mycotoxin content is reduced by at least 50%.
3. The method of claim 1, wherein the carrier is a solvent or surfactant.
4. The method of claim 1, where the carrier is a solvent selected from methanol, ethanol, ethyl acetate, acetone, or a combination thereof.
5. The method of claim 1, wherein the composition further comprises lecanoric acid.

* * * * *